(12) United States Patent
Warnick et al.

(10) Patent No.: US 12,260,440 B1
(45) Date of Patent: Mar. 25, 2025

(54) NON-FUNGIBLE TOKEN TRANSACTION MANAGEMENT SYSTEMS AND METHODS FOR DIGITAL HEALTH DATA

(71) Applicant: United Services Automobile Association (USAA), San Antonio, TX (US)

(72) Inventors: Mark Paxman Warnick, San Antonio, TX (US); Bharat Prasad, San Antonio, TX (US); Carlos JP Chavez, San Antonio, TX (US); Ravi Durairaj, San Antonio, TX (US); Mitzi Ruiz, San Antonio, TX (US); Theresa Marie Matowitz, San Antonio, TX (US); Huihui Wu, Grapevine, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 377 days.

(21) Appl. No.: 17/563,905

(22) Filed: Dec. 28, 2021

(51) Int. Cl.
  *G06Q 30/00* (2023.01)
  *G06F 21/62* (2013.01)
  *G06Q 30/0601* (2023.01)
  *G16H 10/60* (2018.01)
  *H04L 9/32* (2006.01)

(52) U.S. Cl.
  CPC ..... *G06Q 30/0611* (2013.01); *G06F 21/6254* (2013.01); *G06Q 30/0619* (2013.01); *G16H 10/60* (2018.01); *H04L 9/3213* (2013.01)

(58) Field of Classification Search
  None
  See application file for complete search history.

(56) References Cited

U.S. PATENT DOCUMENTS

| | | | | |
|---|---|---|---|---|
| 2009/0192941 | A1* | 7/2009 | Fournier | G16H 15/00 |
| | | | | 707/E17.108 |
| 2017/0329922 | A1* | 11/2017 | Eberting | G16H 40/67 |
| 2019/0287149 | A1* | 9/2019 | Papp | G06Q 20/0658 |
| 2020/0110903 | A1* | 4/2020 | Reilly | H04N 1/4446 |
| 2021/0158722 | A1* | 5/2021 | Vyas | G09B 19/00 |
| 2021/0313069 | A1* | 10/2021 | Williams | G16H 50/30 |
| 2021/0319441 | A1* | 10/2021 | Knobel | H04L 9/3236 |
| 2022/0156339 | A1* | 5/2022 | Grajales | G06Q 30/0623 |

OTHER PUBLICATIONS

"Healthcare, Tech Innovator Patientory is Coming to HIMSS 2019: The startup's CEO Chrissa McFarlane is scheduled to discuss how blockchain technologies can improve healthcare data management", PR Newswire, Feb. 7, 2019 https://dialog.proquest.com/professional/docview/2176707337?accountid=131444 (Year: 2019).*

* cited by examiner

*Primary Examiner* — Ethan D Civan
(74) *Attorney, Agent, or Firm* — Fletcher Yoder, P.C.

(57) ABSTRACT

A health data management method using non-fungible tokens may include receiving, via one processor, digital health data and encrypting or obscuring personal identifying information of the digital health data. The method may then involve using the digital health data with encrypted or obscured personal identifying information to generate a non-fungible token and providing the non-fungible tokens in a marketplace. The method may also involve accepting an offer from a purchaser for the non-fungible token via the marketplace and providing unobscured digital health data or an encryption key to the purchaser of the non-fungible token.

19 Claims, 9 Drawing Sheets

NON-FUNGIBLE TOKEN TRANSACTION MANAGEMENT SYSTEMS AND METHODS FOR DIGITAL HEALTH DATA

BACKGROUND

The present disclosure relates generally to systems and methods related to non-fungible tokens containing digital health data. More specifically, the techniques discussed herein relate to management of digital transactions involving non-fungible tokens containing digital health data.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A non-fungible token (NFT) is a unit of data that may be stored in a distributed ledger and that is unique and/or noninterchangeable such that unique identity and ownership can be confirmed. NFTs can encompass digital artworks (e.g., images and/or audio data), digital collectibles, assets or inventory of video games, digital health data (e.g., medical data and/or fitness data), or programs or instructions to generate physical products by way of example. As the NFT marketplace grows, owners would benefit from management platforms for NFTs.

SUMMARY

Certain embodiments commensurate in scope with the present disclosure are summarized below. These embodiments are not intended to limit the scope of the disclosure, but rather these embodiments are intended only to provide a brief summary of possible forms of present embodiments. Indeed, present embodiments may encompass a variety of forms that may be similar to or different from the embodiments set forth below.

In one embodiment, a health data management system using non-fungible tokens may include a memory storing executable instructions and a processor. The processor may be configured to execute instructions to receive digital health data and generate a non-fungible token responsive to receiving the digital health data, wherein the non-fungible token comprises a record in a distributed ledger and associated content based on the digital health data, wherein the associated content is stored outside of the distributed ledger and wherein a storage location of the associated content of the non-fungible token is determined based on the record.

In another embodiment, a health data management system using non-fungible tokens may include a memory storing executable instructions and a processor. The processor may be configured to execute instructions to receive digital health data for a population of users and anonymize the digital health data. The processor may then aggregate the anonymized digital health data and generate a non-fungible token based on the aggregated, anonymized digital health data.

In yet another embodiment, a health data management method using non-fungible tokens may include receiving, via at least one processor, digital health data and encrypting or obscuring personally identifiable information (PII) of the digital health data. The method may then involve using the digital health data with encrypted or obscured PII to generate a non-fungible token and providing the non-fungible tokens in a marketplace. The method may also involve accepting an offer from a purchaser for the non-fungible token via the marketplace and providing unobscured digital health data or an encryption key to the purchaser of the non-fungible token.

BRIEF DESCRIPTION OF THE DRAWINGS

Various aspects of this disclosure may be better understood upon reading the following detailed description and upon reference to the drawings in which.

DETAILED DESCRIPTION

Figure 1:
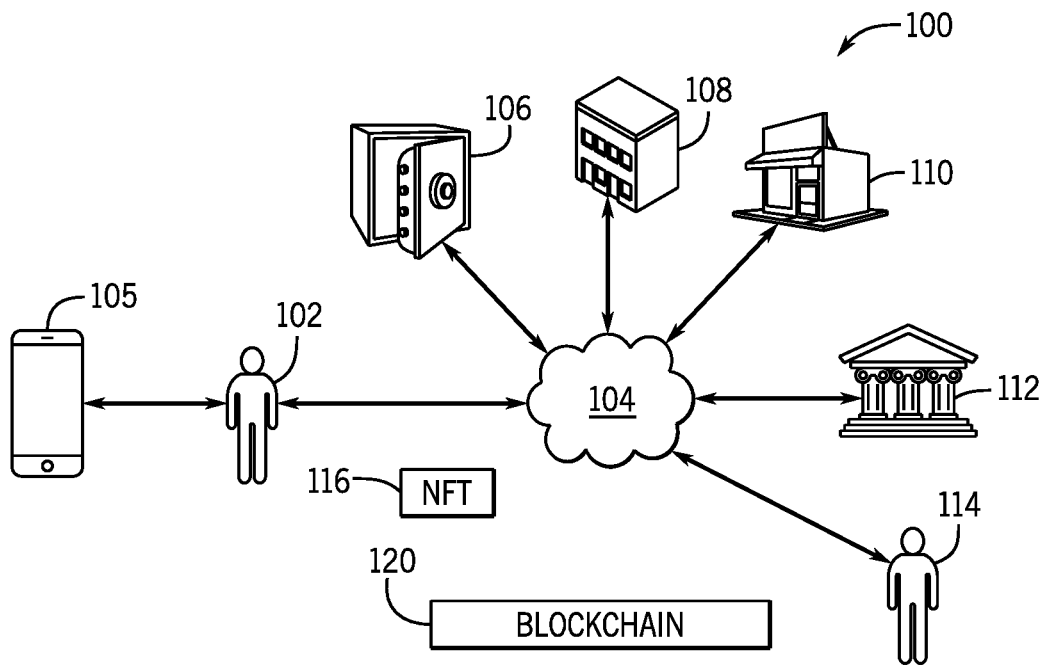
FIG. 1 is a schematic illustration of an environment in which a non-fungible token management system may operate, in accordance with an embodiment.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and enterprise-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As used herein, the term "computing system" refers to an electronic computing device such as, but not limited to, a single computer, virtual machine, virtual container, host, server, laptop, and/or mobile device, or to a plurality of electronic computing devices working together to perform the function described as being performed on or by the computing system. As used herein, the term "medium" refers to one or more non-transitory, computer-readable physical media that together store the contents described as being stored thereon. Embodiments may include non-volatile secondary storage, read-only memory (ROM), and/or random-access memory (RAM).

As used herein, the term "application" refers to one or more computing modules, programs, processes, workloads, threads and/or a set of computing instructions executed by a computing system. Example embodiments of an application include software modules, software objects, software instances and/or other types of executable code.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Present embodiments are generally directed toward non-fungible token (NFT) management techniques that facilitate creation, valuation, authentication, insurance, exchange, and/or storage of NFTs based on user digital health data. The disclosed embodiments facilitate user control of their digital health data-based NFT. In certain embodiments, the user may sell their NFT on a marketplace. These NFTs may also be exchanged in the marketplace to create larger data sets useful for machine learning models related to health data analysis, such as population models or automated insurance evaluations (e.g., health insurance premiums, life insurance policies). By minting NFTs with digital health data, the user may retain control over their personal information and sell their NFTs containing their digital health data in secure, private, tamper-proof transactions.

In certain embodiments, an NFT management system can track incoming digital health data, perform one or more analysis operations using the digital health data, and automatically mint one or more NFTs based on the digital health data, which may include the results of the analysis operations. Thus, in an embodiment, the user need not personally manage the digital health data, and the NFTs may be minted in an arm's length transaction by an NFT manager on behalf of their users. For example, digital health data for an individual user may be generated from a variety of sources, such as electronic medical records, home medical devices, fitness tracking devices, or meal or diet trackers. For example, a user may choose to wear a health tracking device to track their digital health data through an application on a user device (e.g., phone, tablet, computer). In another embodiment, the user may visit a medical institution (e.g., a doctor's office, a laboratory, a clinic) for a health checkup. During the visit, the user may receive digital health data (e.g., medications taken by the user, dates of doctors" visits, current treatments, particular physical conditions, or the like) that they may want to store in a tamper proof and secure means. As such, the user may be interested in generating an NFT containing the digital health data created from the visit. As a way to facilitate self-ownership of personal data, the medical institution may, on behalf of the user, signal to the NFT management system to mint the NFT containing the digital health data acquired by the most recent visit to the medical institution.

The NFT management system, as provided herein, may operate as a clearinghouse for incoming digital health data from a variety of sources. The NFT management system can assess the digital health data according to user preset instructions and generate NFTs accordingly. For example, certain users may have preset instructions to perform a first set of analyses on their digital health data and generate NFTs based on the results. Other users may have preset instructions to perform a different set of analyses on their digital health data and generate NFTs based on the results. Thus, different users within the NFT management system may have a different set of generated NFTs. The disclosed NFT management systems allow granular control of user digital health data.

In some embodiments, the NFT management system may allow users to create and maintain a secure NFT with their digital health data (e.g., health or medical data). Electronic medical records are stored using relatively high security standards that are institutionally maintained. When a user wishes to maintain a copy of their electronic medical records or extract data for additional analysis, the user's home network may not use security protocols that are as stringent as those of the electronic medical records. The use of the disclosed NFT management system permits the user to interact with their digital health data in a personalized manner without having to maintain enhanced security protocols. The NFT management system maintains arm's length transaction between the user and the NFT management system which may afford the user an extra layer of privacy.

The NFT management system may include a portal to allow access to a marketplace, authentication data, insurance information, and insurance purchasing. In an embodiment, the portal of the NFT management system may include a marketplace for the user to sell their NFTs. For example, the user may own an NFT containing their digital health data from a health tracking device. The user may want to sell their NFT to an insurance company as proof of their healthy lifestyle and negotiate a lower insurance premium. As such, the user may access the portal to place their NFT on the marketplace for sale and accept an offer from the highest bidder for their NFT. The user may set up a split payment which may include a transaction fee for up to fifteen different parties. For example, when an original insurance provider generates the NFT on behalf of their user and the user elects to sell the NFT to another insurance provider, the original insurance provider may receive a royalty and/or may be credited for facilitating the sale. In another example, the original insurance provider may store the NFT on behalf of their user and request a transaction fee for storage. As such, transactions on the marketplace may include transaction fees (e.g., a percentage of the NFT cost) to be retained by the original insurance provider for facilitating the sale.

In another embodiment, the insurance provider may access the marketplace to sell NFTs containing large sets of data. Aggregated, anonymized data sets may be useful for improving machine learning or artificial intelligence relating to automated insurance evaluations (e.g., health insurance premiums, life insurance policies). As such, insurance providers may collect digital health data from a group of users (e.g., their users) and remove or obscure personally identifiable information (PII) (e.g., name, birthdate, address) from the collected digital health data. That is, the NFT management system may anonymize the digital health data by removing or obscuring the PII. The NFT management system may aggregate the anonymized digital health data according to a certain attribute (e.g., radiology images relating to stomachs, EKG data for patients over 50) to create a cohesive data set. The NFT management system may generate the NFT based on the cohesive data set and place the NFT on the marketplace for sale. In an embodiment, the NFT management system may determine that the collected digital health data does not contain PII and aggregate the collected digital health data, generate the NFT, and place the NFT for sale on the marketplace.

The NFT management system may execute, using a processor, instructions stored in a memory, for insurance evaluation. The executed instructions may be implemented as part of an analysis engine. For example, the user may set goals with their insurance provider through a program to reduce their health insurance premium. As such, the user may use an analysis engine of the NFT management system to determine if the goals were met. The analysis engine may receive the NFT, analyze the digital health data contained in the NFT, identify whether the goals were met, and output a new insurance evaluation for the user. In an embodiment, the NFT can include a smart contract that executes when the digital health data is indicative of a goal that is met. For example, based on completing a diet or exercise regimen, a lower insurance rate can be automatically triggered. The record of the agreement is maintained in the NFT. Alternatively or additionally, the insurance provider may receive permission from their users to access the portal, access the NFTs of their users, and assess whether the set goals were met by the users. As such, the insurance provider may use the analysis engine of the NFT management system to access the digital health data of the users, determine if the set goals were met, and receive an adjusted insurance evaluation for the users.

The disclosed management systems can create confidence in secondary marketplaces for NFTs and also a marketplace for insuring authenticity or insuring against possible loss. Insuring against possible loss may involve analysis of storage scenarios and storage system integrity (e.g., security from hacking, loss of power, natural disaster) for NFT-associated files.

With the preceding in mind, the following figures relate to various types of generalized system architectures or configurations that may be employed to provide services to an organization in a multi-instance framework and on which the present approaches may be employed. Correspondingly, these system and platform examples may also relate to systems and platforms on which the techniques discussed herein may be implemented or otherwise utilized.

The present disclosure details various embodiments for NFT management. FIG. 1 illustrates an example environment 100 in which a non-fungible token (NFT) management system 104 may operate, in accordance with embodiments described herein. A user 102 can interact with and access the NFT management system 104 via a user device 105. The NFT management system 104 may provide NFT management services to a large number of different organizations or individuals, and may act as a clearinghouse for various types of NFT transactions. For example, the NFT management system 104 may permit one or more NFT transactions of the user 102, a cloud storage system 106, companies and institutions 108, merchants and retailers 110, financial institutions 112, and other users 114. In some embodiments, the companies and institutions 108 may include health insurance companies, life insurance companies, health data companies, or the like. In other embodiments, the merchants and retailers 110 may include health service providers such as doctor's offices, laboratories, clinics, pharmacies, or other medical institutions. The NFT management system 104 facilitates interactions with one or more NFTs 116, which may be stored in the NFT management system 104, transferred via the system 104, accessed via the NFT management system 104, valued by the NFT management system 104, insured via the NFT management system 104, and/or authenticated by the NFT management system 104.

In some embodiments, the NFT management system 104 may facilitate user authentication, which is a technology area that deals with identifying individuals in a system (such as a country, a network, or an enterprise) and controlling access to resources, such as managed NFTs 116, within that system by associating user rights and restrictions with user-associated NFTs and permitting user transactions with NFTs that are owned by the user or that are permitted by an owner of an NFT 116, which may be facilitated in the system 104. In general, the NFT management system 104 may maintain user information for the user 102, companies and institutions 108, merchants and retailers 110, financial institutions 112, other users 114, and the like. In addition, the NFT management system 104 facilitates and maintains NFT identification information and NFT digital data, which can be under user control.

Some of the features that may be provided by the NFT management system 104 includes access to NFT transactions from a mobile application, an embedded application operating on the user device 105, or a web application. In certain embodiments, the NFT management system 104 may securely store identity attributes of the NFT 116 on a blockchain.

As provided herein, the NFT 116 is a token used to represent ownership of one or more unique items. Accordingly, the NFT 116 may refer to a blockchain address or hash associated with the NFT 116 that includes a fixed number of alphanumeric characters generated from a public and private key pair. The NFT 116 may also include digital raw or compressed data representative of the NFT 116 and that is associated with a unique blockchain address. As provided herein, the NFT management system 104 may store the identifier hash, while the digital data of the NFT 116 is stored elsewhere, e.g., the digital data of the NFT 116 (e.g., the image data, the audio data) is stored off-chain. Specifically, the digital data may be digital health data (e.g., medical data, fitness data, treatments, medications doctor's visits) of the user. In embodiments, the NFT management system 104 also stores the digital data of the NFT 116. The NFT 116 may also include metadata (e.g., a JSON file) associated with the digital NFT data. Ownership of the NFT 116 may include ownership of hex values encoding transaction elements, such as function names, parameters, and return values, and that are used to access the data of the NFT 116.

The NFT 116 may, in embodiments, be a type of cryptocurrency that uses smart contracts. However, in contrast to digital coins, which are fungible, each NFT 116 is digitally unique such that no two NFTs 116 are the same. For example, even for items that are multiples of one another (e.g., multiple digital copies of an artwork), each NFT 116 would still have a unique identifier (e.g., a bar code), with only one owner. The intended scarcity of the NFT 116 is set by the creator. A creator may intend to make each NFT 116 completely unique to create scarcity or produce several thousand replicas (each replica having its own unique, non-fungible identifier, similar to an artist print marked as ¹⁄₁₀). Every NFT 116 has an owner of public record that can be verified. In embodiments, NFT creators can retain ownership rights over their own work, and claim resale royalties directly. Thus, the owner of the NFT 116 may have financial arrangements or royalty arrangements that are dictated within the smart contracts of the NFT record.

Creation or minting of an NFT 116 involves confirmation of the NFT 116 as an asset on the blockchain, and the owner's account balance is updated to include that asset. This makes it possible for the NFT 116 to then be traded or verifiably owned. The transactions that confirm the above are added to a block on the chain. The block may be confirmed by everyone in the network as correct. This consensus removes the need for intermediaries because the network verifies the NFT 116 and ownership. As provided herein, the NFT 116 may be created on the Ethereum blockchain. In an embodiment, the NFT 116 may be part of the ERC-721, ERC-1155, and/or EIP-2309 standard.

The NFT management system 104 may employ a blockchain infrastructure to perform NFT management utilized in connection with digital transactions such as NFT minting (e.g., NFT creation), authentication, storage, or financial transactions (e.g., NFT purchasing or exchange, valuation, insurance). In general, blockchains are continuously growing lists of records (e.g., blocks), which are linked and secured using cryptography, for example. By using a blockchain infrastructure that enables the functionality of smart contracts, the methods and systems described herein allow a persistent, replicated, public, and automated database for transactions that involve NFTs.

As such, the embodiments described herein include methods and systems for deployment, maintenance, and interaction with the distributed ledgers and smart contracts to facilitate NFT management for the purpose of performing digital transactions (e.g., financial transactions, exchanges of information). The embodiments described herein may include blockchain techniques, as well as the terminals and servers that operate blockchain nodes, as described herein. Technical advantages of the embodiments described herein also include the use of public and/or private blockchains to perform automated, trusted operations for the purpose of conducting digital transactions involving NFTs 116. The systems described herein allow the performed operations to be transparent and tamper-proof and, thus, may increase the accuracy of, and security with, conducting digital transactions. Moreover, the techniques described herein may also reduce network congestion by, for example, reducing the amount of data transferred between entities that communicate using a network or between two different portions of one entity communicating using a network.

Referring again to FIG. 1, in certain embodiments, the blockchain 120 may be a public or private ledger of all transactions that have been executed in one or more contexts (e.g., negotiable instrument transactions, digital currency transactions, access determinations, instances of providing access, reviews, etc.). The blockchain 120 may grow as completed blocks are added with a new set of transactions by the NFT management system 104. In certain embodiments, a single block is provided from multiple transactions (e.g., multiple statements of authenticity for the NFT 116). In general, blocks are added to the blockchain 120 in a linear, chronological order by one or more computing devices in a peer-to-peer network of interconnected computing devices that execute a blockchain protocol. In short, the peer-to-peer network can be described as a plurality of interconnected nodes, each node being a computing device that uses a client to validate and relay transactions. Each node maintains a copy of the blockchain 120, which is automatically downloaded to the node upon joining the peer-to-peer network. The blockchain protocol provides a secure and reliable method of updating the blockchain 120, copies of which are distributed across the peer-to-peer network, without use of a central authority.

Because all entities on the blockchain network may need to know all previous transactions to validate a requested transaction, all entities must agree on which transactions have actually occurred, and in which order. For example, if two entities observe different transaction histories, they will be unable to come to the same conclusion regarding the validity of a particular transaction. The blockchain 120 enables all entities to come to an agreement as to transactions that have already occurred, and in which order. In short, and as described in further detail below, a ledger of transactions is agreed to based on the amount of work required to add a transaction to the ledger of transactions (e.g., add a block to the blockchain 120). In certain embodiments, the blockchain 120 may also employ other protocols. In this context, the work is a task that is difficult for any single node (e.g., computing device) in the peer-to-peer network to quickly complete, but is relatively easy for a node (e.g., computing device) to verify.

The peer-to-peer network includes miners (e.g., computing devices) that add blocks to the blockchain 120 based on the blockchain protocol. In general, multiple miners validate transactions that are to be added to a block, and compete (e.g., perform work, as introduced above) to have their block added to the blockchain 120. Validation of transactions includes verifying digital signatures associated with respective transactions. For a block to be added to the blockchain 120, a miner must demonstrate a proof of work before their proposed block of transactions is accepted by the peer-to-peer network, and is added to the blockchain 120. In certain embodiments, the blockchain protocol includes a proof of work scheme that is based on a cryptographic hash function (CHF). In general, the CHF receives information as input, and provides a hash value as output, the hash value being of a predetermined length. In certain embodiments, the hash value is a one-way hash value, in that the hash value cannot be "un-hashed" to determine what the input was. In certain embodiments, the blockchain protocol may require multiple pieces of information as input to the CHF. For example, the input to the CHF may include a reference to the previous (most recent) block in the blockchain 120, details of the transaction(s) that are to be included in the to-be-created block, and a nonce value (e.g., a random number used only once).

Multiple nodes may compete to hash a set of transactions and provide the next block that is to be added to the blockchain 120. In certain embodiments, the blockchain protocol provides a threshold hash to qualify a block to be added to the blockchain 120. For example, the threshold hash may include a predefined number of zeros (0s) that the hash value must have at the beginning (e.g., at least the first four characters of the hash value must each be zero). The higher the number of zeros, the more time-consuming it is to arrive at a qualifying hash value.

In accordance with the blockchain protocol, each miner in the peer-to-peer network receives transaction information for one or more transactions that are to be included in a block that is to be added next in the blockchain 120. Each miner provides the reference to the previous (most recent) block in the blockchain 120, details of the transaction(s) that are to be included in the to-be-created block, and the nonce value to the CHF to provide a hash value. If the hash value does not meet the threshold hash (e.g., the first four characters of the hash value are not each zero), the miner starts again to provide another hash value. If the hash value meets the threshold hash (e.g., at least the first four characters of the hash value are each zero), the respective miner successfully created the next block that is to be added to the blockchain 120. Consequently, the respective miner's block is broadcast across the peer-to-peer network. All other miners cease work (because one miner was already successful), and all copies of the blockchain 120 are updated across the peer-to-peer network to append the block to the blockchain 120. Each miner may be required to produce hundreds or thousands of hash values, before any one miner provides a qualifying hash value (e.g., at least the first four characters of the hash value are each zero).

In certain embodiments, the distributed ledger (or blockchain 120) system may include one or more sidechains. A sidechain may be described as a blockchain 120 that validates data from other blockchains 120. In certain embodiments, a sidechain enables ledger assets (e.g., a digital currency) to be transferred between multiple blockchains 120. In certain embodiments, the blockchain 120 may be a public blockchain, such that data stored on the blockchain 120 is generally accessible. In other embodiments, the blockchain 120 may be a private blockchain, such that the stored data is accessible only to authorized individuals and/or processes on the blockchain 120. In certain embodiments, the blockchain 120 may also be a hybrid of public and private blockchains. For example, the NFT management system 104 may utilize a privately managed, but publicly readable blockchain 120. In this manner, some identity information about a user 102 may be stored in a sidechain. In certain embodiments, the NFT management system 104 may store multiple different NFTs 116 associated with respective different users 102.

Figure 2:
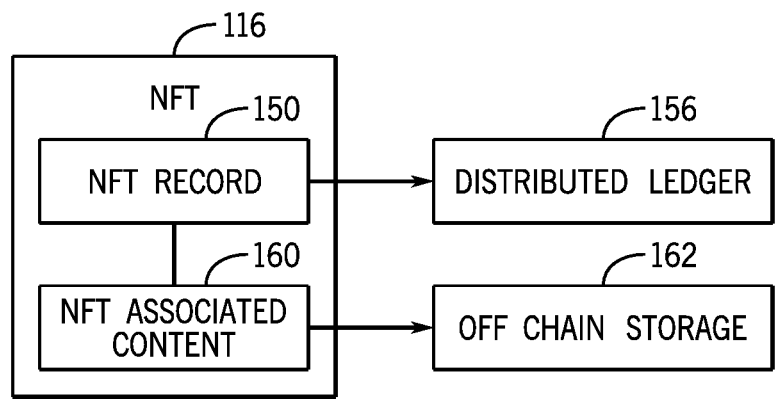
FIG. 2 is a block diagram of non-fungible token storage arrangement, in accordance with an embodiment.

FIG. 2 shows an example NFT 116 and storage arrangement that includes an NFT record 150 (e.g., a token, such as a hash) that is stored and validated in a distributed ledger 156 (e.g., a blockchain record). The NFT record 150 includes ownership information and transaction histories. The NFT record 150, as discussed herein, includes a unique identification that uniquely identifies NFT associated content 160, which can be one or more files that includes the digital data of the NFT 116, such as text, image files, video files, audio files, game item files, or any suitable NFT associated content 160. For example, the NFT associated content 160 may include digital health data such as medical charts, fitness data, medical evaluations, anonymized data, medical records, or the like. The NFT associated content 160 may include metadata. While the NFT record 150 is stored in the distributed ledger 156, e.g., a blockchain, storing the NFT associated content 160 in a distributed ledger format may be prohibitively expensive, particularly for larger files. Accordingly, NFT associated content 160 can be stored in an off-chain storage 162. The location of the off-chain storage 162 at the time the NFT 116 was minted can be specifically referred to in the NFT record 150. For example, the NFT record 150 can include a URL link to the NFT associated content 160.

In certain embodiments, the NFT 116 may include seed information that populates variables for a fixed NFT generation algorithm (e.g., an image or audio generation algorithm). Each seed can be a hexadecimal string generated in a random or pseudorandom manner at the time the token is minted. However, the algorithm is fixed, such that using a specific seed provides identical result each time. In embodiments, the seed can be stored as part of the NFT record 150 on the distributed ledger 156. The algorithm can be stored as part of the NFT record 150 and/or stored in off-chain storage 162. In this manner, the NFT associated content 160 can be generated on demand using the algorithm and the seed. This may permit greater on-chain storage capabilities, without requiring storage of large data files that are expensive to mint. The seed, and algorithm in embodiments, can be relatively small and inexpensive to record in the distributed ledger 156.

Off-chain storage 162 solutions are typically set by the minter of the NFT 116, and can vary in quality and security. For example, the off-chain storage can be a website, and the NFT record 150 can refer to an HTTP address. However, website access can be shut down if the account holder abandons the site. Further, the owner of the website can alter or replace the original NFT associated content 160. Other storage solutions may be longer-term or more stable, such as storage in InterPlanetary File System (IPFS) or Arweave. In IPFS storage, any added file is given its own unique identifier that acts as a permanent record of the file. Therefore, NFT associated content 160 stored off-chain in an IPFS storage may have a unique token identifier as part of the NFT record 150 and may also have a storage record, such as a content identifier (CID), as part of the stored file in the off-chain storage 162. Accordingly, different NFTs 116 may have different data persistence or mutability based on the quality of the off-chain storage 162. In an embodiment, NFT associated content 160 may be fixed at the time of minting of the NFT 116. However, in other embodiments, the NFT associated content 160 may be dynamic and updates when new digital health data may be received. The parameters of the updating may be set in the self-executing contract of the NFT 116. The NFT management system 104 may act as an arbiter or oracle of the terms of the contract.

The NFT purchaser may wish to store the NFT 116 privately to create scarcity of the NFT associated content 160. In an embodiment, the NFT management system 104 can include off-chain storage 162 with controlled or user-set access for managed NFTs 116. Thus, the NFT management system 104 addresses uncertainties caused by an unsecured link between the NFT record 150 and the NFT associated content 160.

Further, the purchaser of the NFT 116 may be at arm's length from the original creator (minter) of the NFT 116 and may not have any way of contacting the creator to alter the storage arrangements or authenticate the NFT associated content 160. Disclosed embodiments of the NFT management system 104 include improved authentication of the NFT associated content 160 for downstream purchasers of the NFT 116, which in turn may permit controlled storage of an authenticated copy of the NFT associated content 160. A user 102 of the NFT management system 104 may wish to control storage of a purchased NFT 116 or have access to an authenticated copy of the associated content 160 that is stored in a secure storage location.

Figure 3:
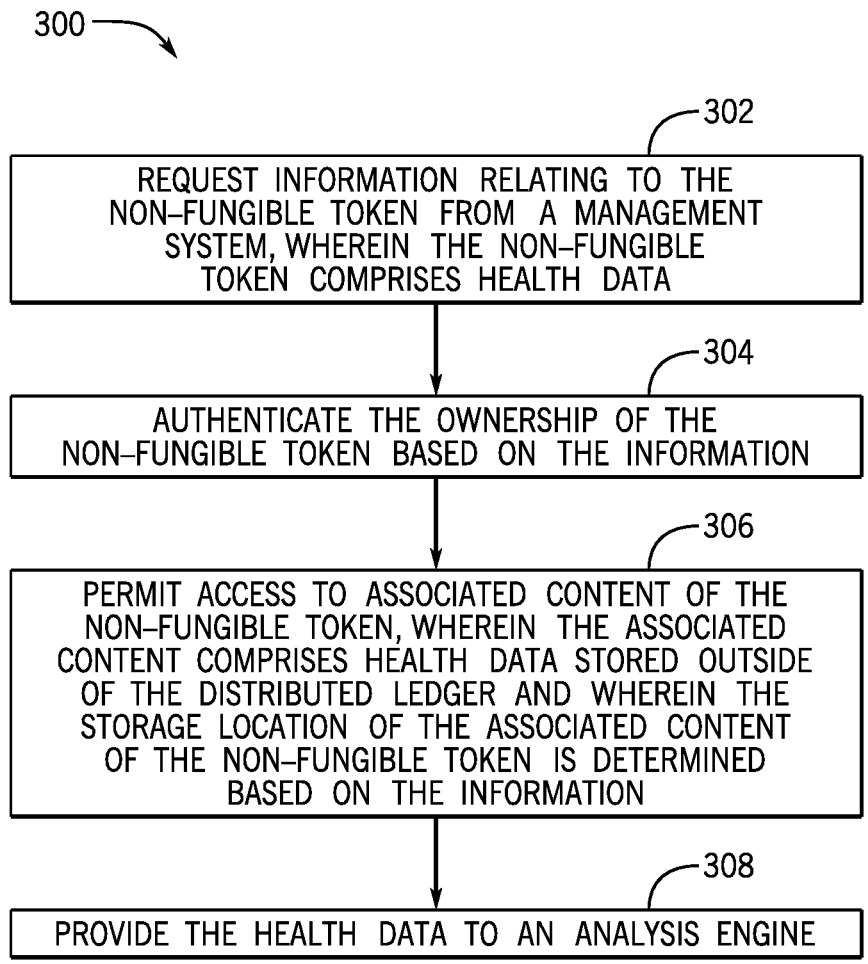
FIG. 3 is a flow diagram of an example method of non-fungible token management, in accordance with an embodiment.

FIG. 3 is a flow diagram of a method 300 of NFT management. Although the following description of the method 300 is described as being performed by the NFT management system 104, the method 300 may be performed by any suitable computing system and may include communication with other devices or entities as provided herein. In addition, although the method 300 is described in a particular order, it should be understood that the method 300 may be performed in any suitable order.

The method includes receiving (e.g., by the NFT management system 104) a request for information relating to the NFT 116 recorded in a distributed ledger 156. The request may include a reference to the NFT record 150, which can be accessed via a distributed ledger 156 (block 302). The received request may trigger an owner authentication step (block 304) which may require 1) the identity of the requestor to be verified and 2) the requestor to be the owner of the NFT 116 based on the NFT record 150.

The method 300 may include a step of accessing, or attempting to access, NFT associated content 160 (block 306). The NFT associated content 160 may include digital health data of the user 102 located outside of the distributed ledger 156. The digital health data of the user 102 may include medical charts, fitness data, medical evaluations, aggregated data, anonymized data, medical records, or the like. In some embodiments, the digital health data may be generated by the user 102 via a health tracking device such as a smart watch or a step tracker. In other embodiments, the digital health data may be generated by a visit to the doctor's office for a checkup or by answering questions on a medical questionnaire. Still in other embodiments, the digital health data may be aggregated, anonymized digital health data from a population of users that may be useful for machine learning modeling. The NFT associated content 160 may also include metadata. The NFT associated content 160 may be stored in an off-chain storage 162. The location of the off-chain storage 162 may be determined at the time the NFT 116 was minted and specifically referred to in the NFT record 150. As such, the storage location of the NFT associated content 160 may be determined based on the NFT record 150.

While file systems such as IPFS may provide secure storage, IPFS files are public and accessible. In addition, the NFT record 150, which is set by the NFT creator, may refer to an intermediate gateway to the IPFS file rather than the IPFS hash itself. The intermediate gateway may have a greater chance of being unstable or unmaintained. Further, the file in the IPFS is hosted by a node, which may no longer be hosted. Therefore, the IPFS file for the NFT associated content 160 may also be inaccessible over time. In one example, the link referred to in the NFT record 150 may be broken. Thus, the method 300 may generate a notification that the NFT 116 cannot be managed by the system 104 based on a broken relationship between the NFT record 150 and the associated content 160. Further, the NFT management system 104 may offer solutions for repairing the broken link between the NFT record 150 and the associated content 160 via updated authentication and/or offers to host the NFT associated content 160 in storage of the system 104. In another example, the NFT management system 104 may access the NFT associated content 160 from the link and compare the NFT associated content 160 to a thumbnail or image of the NFT 116 in the marketplace. If there is a mismatch, indicating that the hosted NFT 116 does not match the image that is advertised for sale, the NFT management system 104 can trigger an alert or flag. In one example, the NFT management system 104 may block sale of a particular NFT 116 that has a broken link and/or an image (or other digital data) mismatch between the advertised image and the image in the referenced link.

The NFT management system 104 assesses the NFT record 150 to determine if, for example, the NFT record 150 includes references to IPFS hash (or other direct reference to a file identifier of the off-chain storage 162) or to an intermediate URL and may assess a first storage value and a second storage value, respectively based at least in part on storage assessment. The first storage value can be a higher weight for strong or stable storage which the second storage value can be a lower weight for weaker storage. The storage may be evaluated for potential hacking, loss of power, natural disaster, and so forth.

The NFT management system 104 may provide the NFT associated content 160 to an analysis engine of the owner for processing (block 308). In some embodiments, the analysis engine may use the NFT associated content 160 and the storage location (e.g., an assigned storage value linked to the storage location) for an insurance policy evaluation (e.g., health insurance and/or life insurance). That is, the analysis engine may generate an insurance evaluation based on the NFT associated content 160 and output the analysis to the NFT management system 104. For example, an insurance provider may offer a discount on premiums if the user meets certain health goals, such as getting an annual physical, walking 10,000 steps a day, or the like. In some embodiments, the insurance provider may generate the NFT 116 on behalf of their users 102 containing digital health data of the user 102. The insurance provider may request the NFT management system 104 to provide the NFT associated content 160 the analysis engine to determine if the set goals were met and generate an insurance policy evaluation. In some embodiments, the analysis engine may determine if the NFT associated content 160 meets predetermined conditions and generate an insurance policy evaluation. As such, the analysis engine may output an adjusted insurance policy evaluation to the NFT management system 104 based on the NFT associated content 160.

In another embodiment, the analysis engine may use the NFT associated content 160 and the storage location to determine if the NFT 116 may be placed on a marketplace for sale. For example, the insurance provider may collect the digital health data of their users 102 to create larger data sets. The insurance provider, through the NFT management system 104, may remove or obscure personally identifiable information (PII) from the aggregated digital health data. The insurance provider may request the NFT management system 104 to mint an NFT containing the aggregated, anonymized digital health data set for sale on the marketplace. As such, the analysis engine may access the NFT associated content 160 and the storage location to analyze the aggregated, anonymized digital health data to determine if PII is present. In some embodiments, the analysis engine may flag the NFT 116 as ineligible for marketplace transactions and signal to the NFT management system 104 to take the NFT 116 off the marketplace.

In an embodiment, the analysis engine may assess the NFT associated content 160 and flag the NFT 116 as requiring attention from the user 102. In some embodiments, the analysis engine may receive digital health data (e.g., electronic medical record) from a medical institution, perform an analysis on the digital health data, and identify gaps in digital health data. Gaps in the digital health data may include missed doctor visits or medications, abnormal conditions, or the like. The analysis engine may flag the NFT 116 as having gaps and output the gaps to the NFT management system 104.

Figure 4:
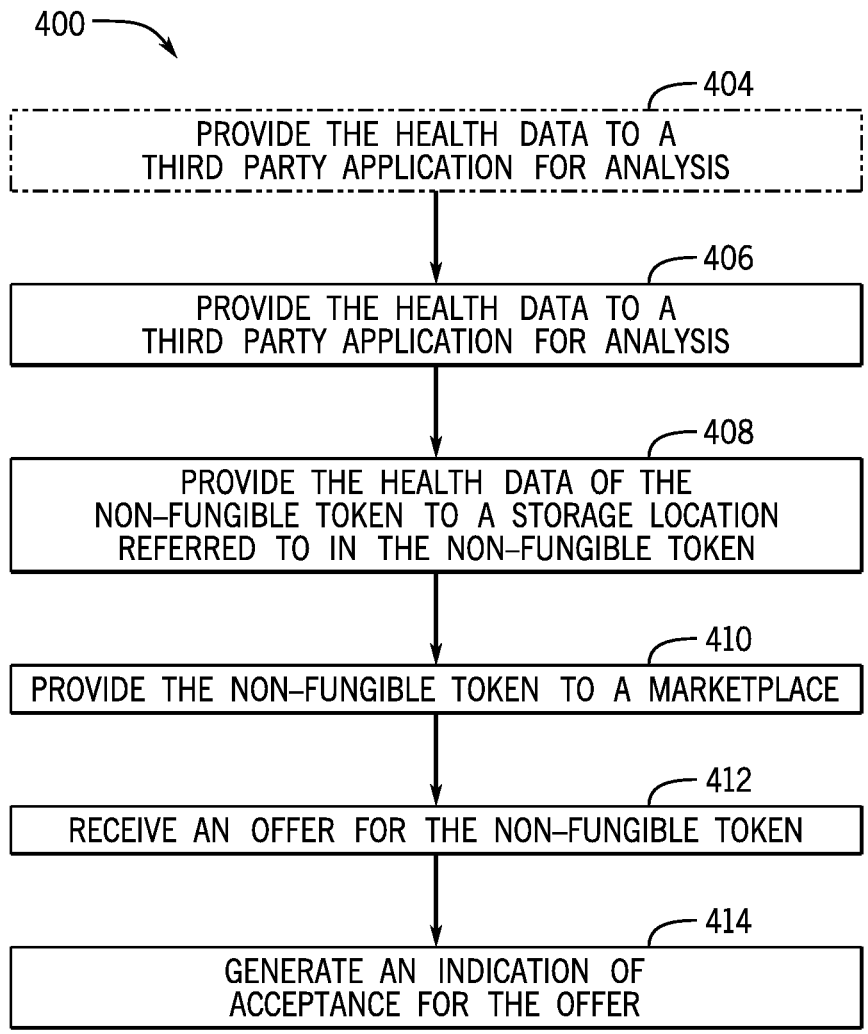
FIG. 4 is a flow diagram of an example method of non-fungible token management, in accordance with an embodiment.

FIG. 4 is a flow diagram of a method 400 of NFT management. Although the following description of the method 400 is described as being performed by the NFT management system 104, the method 400 may be performed by any suitable computing system and may include communication with other devices or entities as provided herein. In addition, although the method 400 is described in a particular order, it should be understood that the method 400 may be performed in any suitable order.

The method includes receiving (e.g., by the NFT management system 104) digital health data that is generated via a health tracking device of the user 102. For example, the user 102 may wear a health tracking device to monitor one or more physical conditions (e.g., heart rate, sleeping patterns, blood oxygen levels) and transmit the digital health data to the user device 105 for storage. For example, the user 102 may wear a health tracking device such as a smart watch or a step tracker and continuously generate digital health data to be stored in a third party application on the user device 105. In another example, the user 102 may use their user device 105 to generate digital health data to be stored in the third party application. Still in another example, the user 102 may generate digital health data by manually inputting digital health data (e.g., missing data points) into the third party application. By storing the digital health data in the third party application, the user 102 may maintain control over their digital health data and create an arm's length transaction between the NFT management system 104 and the user 102. As such, the user 102 may request the third party application to analyze the stored digital health data and output the analysis (block 404).

The method 400 includes a step of creating or minting the NFT 116 based on the stored digital health data. The NFT management system 104 may generate an NFT 116 in which the NFT associated content 160 includes the digital health data stored on in the third party application. In some embodiments, the user 102 may indicate to the NFT management system 104 the subset of digital health data to include in the NFT 116. For example, the user 102 may want to include a set of heart data generated in the month of October. As such, the user 102 may indicate this selection through the third party application to the NFT management system 116. In some embodiments, the third party application may automatically signal to the NFT management system 104 to mint the NFT 116 based on the NFT associated content 160 (block 406). For example, the third party application may be set to collect and store digital health data for one year before transmitting the data to the NFT management system 104 for NFT generation.

As described above, the creation or minting of an NFT 116 includes confirmation of the NFT 116 as an asset on the blockchain. This makes it possible for the NFT 116 to then be traded or verifiably owned. The NFT 116 may include the NFT record 150 which uniquely identify the NFT associated content 160. Specifically, the location of the off-chain storage 162 may be determined at the time the NFT 116 is minted and specifically referred to in the NFT record 150. As such, the NFT management system 104 may provide the digital health data of the NFT associated content 160 to the storage location referred to in the NFT record 150 (block 408). In some embodiments, the NFT associated content 160 may have PII removed or obscured and may be stored in IPFS or Areweave.

In some embodiments, the user 102 may decide to trade their NFT 116. In an example, the user 102 may choose to switch insurance providers and want to provide the digital health data contained on the NFT 116 to a new insurance provider. A quick, secure, and easy method involves trading the NFT 116 containing their digital health data to the new insurance provider. As such, the user 102 may access the portal to place the NFT 116 on the marketplace for trading to the new insurance provider (block 410). The marketplace may be accessed by companies and institutions 108, merchants and retailers 110, financial institutions 112, or the like. In some embodiments, the user 102 may set a minimum bidding price and the NFT 116 may be sold if the bidding price is higher than the minimum bidding price. In other embodiments, the user 102 may require the NFT management system 104 to verify that the purchaser meets certain preset criteria before placing a bid on the NFT 116. For example, the user 102 may want a certain insurance provider to bid on the NFT 116 and, as such, may require the purchaser to verify their identity with a passcode before placing a bid.

On the marketplace, the NFT 116 may be identified via an image (or other digital data) or the NFT record 150. The user 102 may select an advertising image, a string of text, or other digital data to represent their NFT 116 on the marketplace. For example, the NFT management system 104 may compare the advertised image of the NFT 116 with the NFT record 150 containing a reference link and a reference image to determine if the sale of the NFT 116 may continue. In some embodiments, the NFT management system 104 may perform a check of scanning the NFT record 150 to ensure that the NFT 116 has the desired identification number and is not a slightly modified version. For example, NFT record 150 consisting of alphanumeric strings can be searched using a text-based search. In other embodiments, the NFT management system 104 may test the URL link to ensure that the relationship between the NFT record 150 and the NFT associated content 160 is not broken. As describe above, the NFT management system 104 may send a notification that the NFT 116 may not be managed based on a broken relationship offer solutions for repairing the relationship between the NFT record 150 and the NFT associated content 160.

While the NFT 116 may be on the marketplace, the user 102 may receive an offer for the NFT 116 (block 412). In some embodiments, the purchaser may be the companies and institutions 108, merchants and retailers 110, financial institutions 112 of FIG. 1. For example, the purchaser may be a health insurance provider to facilitate determination of the health insurance costs (e.g., health insurance premiums).

In one embodiment, the user 102 may accept the offer for the NFT 116 and indicate to the NFT management system 104 to accept the offer (block 414). As described above, the user 102 may have a financial arrangement or royalty arrangement with the insurance provider regarding the sale of the NFT 116. For example, the insurance provider may mint the NFT 116 on behalf of the user 102 and incur charges during the minting process. In another example, the insurance provider incur charges for storing the NFT 116 on behalf of the user 102. In some embodiments, the user 102 and their insurance provider may have an agreement as to how the proceeds of the NFT 116 sale may be split between the parties. As such, the user 102 may set up split payments before the NFT 116 may be sold delegating the splitting of the proceeds. That is, the original insurance provider may receive a transaction fee for facilitating the sale of the NFT 116 or for storing the NFT 116. Specifically, when the user 102 elects to sell their NFT 116 to another insurance provider, the original insurance provider may receive royalties to recover the cost of minting or storing the NFT 116.

Figure 5:
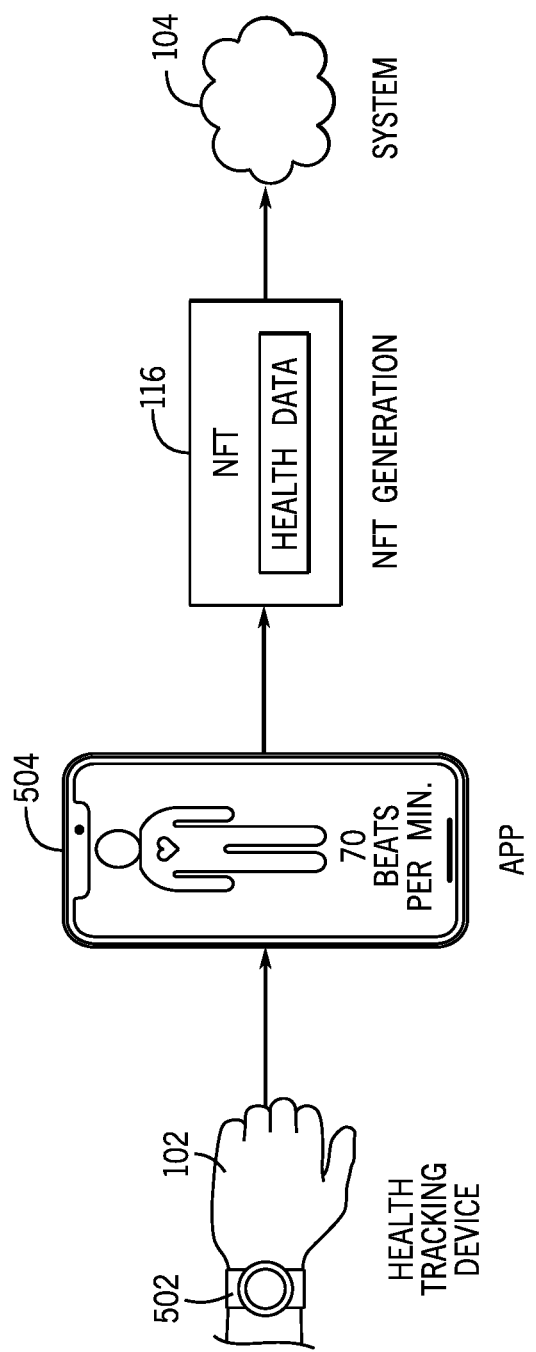
FIG. 5 is a schematic illustration of non-fungible token generation and management arrangement with respect to the example method of FIG. 4, in accordance with an embodiment.

In an embodiment, as illustrated in FIG. 5, the NFT management system 104 may create and store the NFT 116 based on digital health data of the user 102 from the health tracking device. The user 102 may wear the health tracking device (e.g., a smart watch 502) to generate digital health data throughout the day. In some embodiments, the user 102 may simply use their user device 105 to generate digital health data. For example, the user 102 may be interested in tracking their total steps in a day and may choose to carry a smart phone with them in order track their steps.

The user 102 may store their digital health data in the third party application 504 on the user device 105. The third party application 504 may ask the user 102 to input biometric data including height, weight, fitness goals, or the like. The third party application 504 may allow the user 102 to select the type kind of digital health data to be tracked, such as sleep data, fitness data, heart rate data, or a combination thereof. In some embodiments, the third party application 504 may analyze the digital health data to determine a health trend of the user 102, such as whether the user is hitting fitness or sleep goals. In some embodiments, the third party application 504 may monitor certain conditions or physical aspects, such as heart beat or blood oxygen levels, and may transmit a notification to the user 102 when physical conditions go above or below a predetermined threshold. That is, the third party application 504 may send alerts to the user 102 regarding abnormal conditions and flag these abnormal conditions in the stored digital health data. Accordingly, as provided herein, the digital health data may include one or more of raw data from the health tracking device or processed data from the third party application 504. For example, the health tracking devices may detect heart rate data over a period of time, provide the heart rate data to the third party application 504 and perform a proprietary analysis of the heart rate data to generate a processed output. While the algorithm of the processed output may not be provided, the third party application 504 may provide an image of the processed output to the NFT management system 104.

To protect the privacy of the user 102, the third party application 504 may provide the digital health data of the user 102 to the NFT management system 104 for NFT generation. For example, the user 102 may indicate to the third party application 504 to take the stored digital health data and transmit it to NFT management system 104 for NFT creation or minting. Additionally or alternatively, the user 102 may indicate to the NFT management system 104 to encrypt the digital health data before NFT creation. By operating through the third party application 504, the user 102 maintains an additional layer of privacy or an arm's length transaction with the NFT management system 104 for NFT generation. After receiving such indication from the user 102, the NFT management system 104 may take the stored digital health data and mint the NFT 116 with the NFT record 150 in the distributed ledger 156 and the NFT associated content 160 stored in the off-chain storage 162. The NFT associated content 160 may be the digital health data of the user 102, metadata, or a combination thereof. In another embodiment, the NFT management system 104 may mint the NFT 116 with encrypted digital health data of the user 102, which may provide an additional layer of protection for the user 102.

After the NFT 116 is minted, the NFT management system 104 may store the NFT associated content 160 according to the NFT record 150. For example, the NFT management system 104 may store the associated digital health data outside of the distributed ledger 162 in accordance to the NFT record 150. The NFT management system 104 may store the NFT 116 in the system, the cloud storage system 106, or the like. In other embodiments, the NFT management system 104 may place the NFT 116 into the marketplace for trading.

Figure 6:
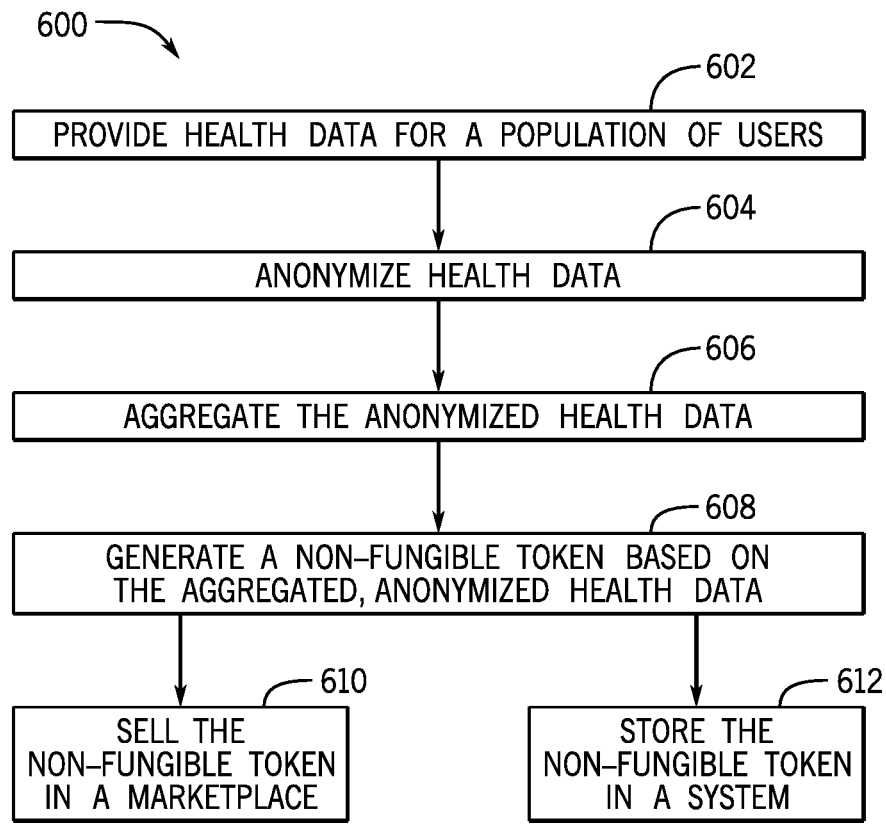
FIG. 6 is flow diagram of an example method of non-fungible token management, in accordance with an embodiment.

FIG. 6 is a flow diagram of an example method 600 of NFT management.

Although the following description of the method 600 is described as being performed by the NFT management system 104, the method 600 may be performed by any suitable computing system and may include communication with other devices or entities as provided herein. In addition, although the method 600 is described in a particular order, it should be understood that the method 600 may be performed in any suitable order.

The method 600 includes a step of receiving. (e.g., by the NFT management system 104) digital health data for a population of users (block 602). For example, the merchants and retailers 110 (e.g., such as a medical institution) may have a collection of heart data that may be useful for machine training or artificial intelligence in facilitating automated insurance evaluations. In such cases, it may be useful for the institution to create an NFT 116 with the heart data for sale on the marketplace or storage in the NFT management system 104. In another example, an insurance provider may collect digital health data from the population of users (e.g., their users) and provide the digital health data to the NFT management system 104 for NFT 116 creation or minting (block 602). The NFT management system 104 may receive, through the analysis engine, the digital health data from the population of users. The analysis engine may anonymize the digital health data to remove or obscure PII such as patient name, unique identifiers, or any information that permits the identity of an individual to whom the information applies to be reasonable inferred by either direct or indirect means (block 604). For example, the NFT management system 104, via the analysis engine, may take the heart data and remove both the doctor and patient's name to protect patient identity.

The anonymized digital health data may be aggregated to remove or obscure PII (block 606). For example, the medical institution may have anonymized digital health data (e.g., heart data from a group of users with PII removed or obscured) that may be useful in insurance evaluation. The medical institution may signal to the NFT management system 104 to aggregate the anonymized digital health data for NFT creation. In some embodiments, the NFT management system 104 may prompt the user 102 to inspect the aggregated, anonymized digital health data to ensure PII has been properly removed or obscured. In other embodiments, the NFT management system 104 may encrypt the aggregated, anonymized digital health data. The medical institution, through the NFT management system 104, may select a stock image as the identifying image for the NFT 116 data set rather than selecting an image from the aggregated, anonymized digital health data set to protect the privacy of their patients. In another example, the NFT management system 104 may simply provide string of text (e.g., name) as the identifier of aggregated, anonymized digital health data rather than the stock image.

The NFT management system 104 may use the aggregated, anonymized digital health data and create or mint the NFT 116 (block 608). As such, the NFT associated content 160 contains the aggregated, anonymized digital health data. Such dataset may be useful for companies and institutions 108 or merchants and retailers 110 to improve machine learning models and artificial intelligence to improve automated insurance evaluations.

In some embodiments, the NFT management system 104 may place the NFT 116 onto a marketplace for sale (block 610). As described above at block 410, the NFT 116 may be placed on the marketplace for bidding. For example, the companies and institutions 108 (e.g., insurance provider) may place the NFT 116 containing aggregated, anonymized digital health data on the marketplace for sale. The insurance provider may set a minimum bidding price and signal to the NFT management system 104 to sell the NFT 116 if an offer price may be higher than the minimum bidding price. In another embodiment, the insurance provider may require a purchaser to meet certain verification before allowing the NFT management system 104 to release the NFT 116 for sale.

In other embodiments, the NFT management system 104 may store the NFT 116 in the NFT management system 104 or the cloud storage system 106 (block 612). For example, the insurance provider may determine that the NFT 116 may not be ready for the marketplace and may decide to keep the NFT 116 in storage (e.g., database, cloud storage 106). In another example, the user 102 may decide to store the NFT 116 in the NFT management system 104.

As described above, the NFT management system 104 may determine the storage location of the associated content 160 of the NFT 116 based on the NFT record 150. As such, the NFT management system 104 may place the aggregated, anonymized digital health data in the storage location referred to in the NFT record 150. The NFT management system 104 may store the NFT associated content 160 in the off-chain storage 162 referred to in the NFT record 150. In some embodiments, the NFT management system 104 may determine that the aggregated, anonymized data is secure and store the NFT associated content 160 in IPFS or Areweave.

Figure 7:
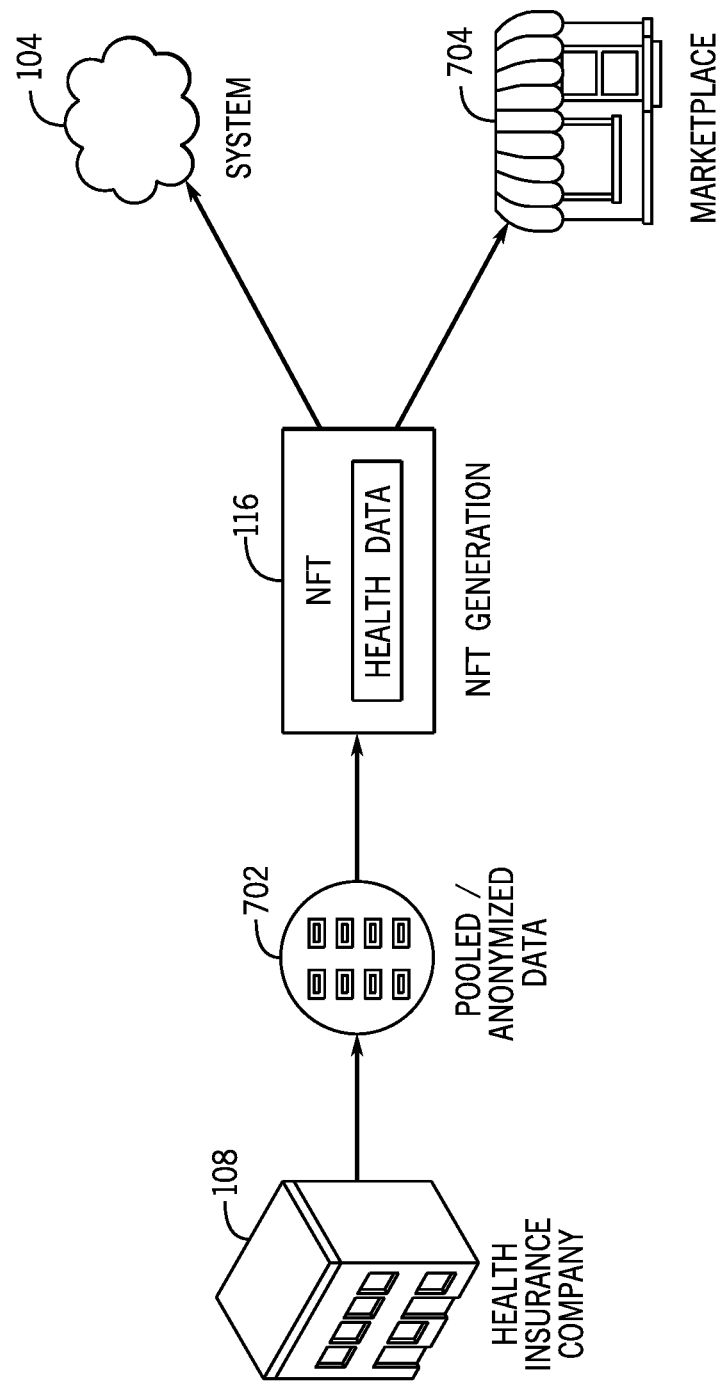
FIG. 7 is a schematic illustration of non-fungible token generation and management arrangement with respect to the example method of FIG. 6, in accordance with an embodiment.

In an embodiment, as illustrated in FIG. 7, the NFT management system 104 may receive aggregated, anonymized digital health data and create the NFT 116 containing such data. For example, the companies or institutions 108 (e.g., a health insurance company) may generate digital health data for a population of users (e.g., their users 102). For example, the health insurance company may ask their users 102 for permission to store the digital health data of the user 102 in the NFT management system 104. In an embodiment, the NFT management system 104 may store the digital health data according to select attributes, such as heart data, walking data, sleep data or the like. In other embodiments, the NFT management system 104 may separate the digital health data based on other factors such as age, health conditions, insurance policy, or the like. Still in other embodiments, the NFT management system 104 may separate the data according to metadata of the digital health data. The NFT management system 104 may aggregated the digital health data according to the select attributes, factors, metadata, or a combination thereof.

To protect the privacy of their users, the health insurance company may signal to the NFT management system 104 to aggregate and anonymize the received digital health data. As described above, the NFT management system 104 may also remove or obscure PII from the digital health data. The NFT management system 104 may aggregate the anonymized digital health data in order to create a cohesive data set intended to facilitate automated insurance evaluations for machine learning or artificial intelligence. In some embodiments, The NFT management system 104 may encrypt the aggregated, anonymized digital health data for an extra layer of protection.

The health insurance company may choose to create or mint the NFT 116 containing the aggregated, anonymized digital health data 702. As such, the NFT associated content 160 may contain the aggregated, anonymized digital health data 702. The NFT record 150 may contain the metadata related to the aggregated, anonymized digital health data 702, a URL link, or other information necessary for identifying the pooled, aggregated health data.

In other embodiments, the NFT management system 104 may place the NFT 116 in the system (e.g., the NFT management system 104, the cloud storage system 106) for safe keeping (block 612). For example, the user 102 may determine that the NFT 116 may be kept for future user or may not be ready for the marketplace. As such, the user 102 may signal to the NFT management system 104 to keep the NFT 116 in storage (e.g., database, cloud storage, or the like).

The NFT management system 104 may determine the storage location of the NFT associated content 160 based on the NFT record 150. As such, the NFT management system 104 may place the aggregated, anonymized digital health data in the storage location referred to in the NFT record 150. The NFT management system 104 may store the NFT associated content in the off-chain storage 162 referred to in the NFT record 150. In some embodiments, the NFT management system 104 may determine that the aggregated, anonymized data may be secure and store the NFT associated content 160 in IPFS or Areweave.

In some embodiments, the NFT management system 104 may place the NFT 116 onto a marketplace 704 for bidding. In an embodiment, the user 102 may decide to sell the NFT 116 when changing insurance providers. As such, the user may the NFT 116 containing their digital health data on the marketplace 704 for bidding. The user 102 may set the minimum bidding price for the NFT 116 and signal to the NFT management system 104 to sell the NFT 116 when the offer price may be higher than the minimum bidding price. In another embodiment, the user 102 may require the purchaser to meet certain criteria before allowing the NFT management system 104 to release the NFT 116 for sale.

Figure 8:
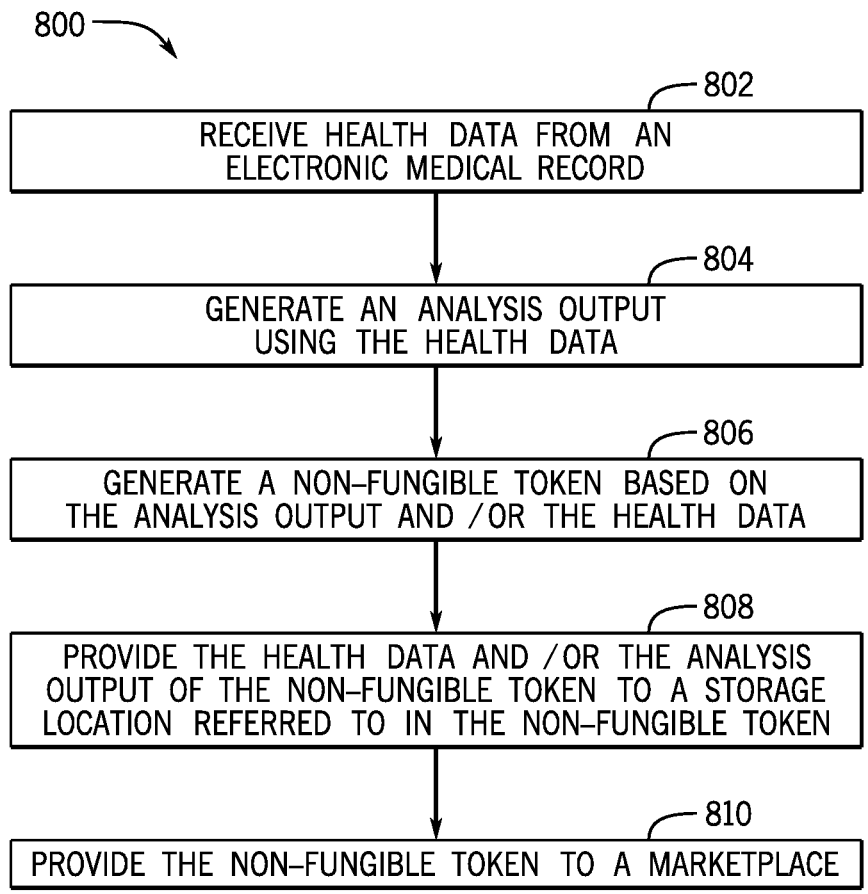
FIG. 8 is flow diagram of an example method of non-fungible token management, in accordance with an embodiment.

FIG. 8 is a flow diagram of a method 800 of NFT management. Although the following description of the method 800 is described as being performed by the NFT management system 104, the method 800 may be performed by any suitable computing system and may include communication with other devices or entities as provided herein. In addition, although the method 800 is described in a particular order, it should be understood that the method 800 may be performed in any suitable order.

The method 800 includes a step of receiving (e.g., by the NFT management system 104) digital health data from an electronic medical record (block 802). The NFT management system 104 may receive (e.g., by the analysis engine) digital health data from the companies or institutions 108 (e.g., insurance provider), merchants and retailers 110, financial institutions 112, the user 102 or other users 114, or the like. The electronic medical record may consist of information from an annual checkup, bloodwork, emergency room visit, medications, treatments, or any combination thereof.

In an embodiment, the analysis engine may analyze the digital health data to generate an analysis output (block 804). For example, the digital health data may be medical records of a user 102 and the analysis engine may analyze the medical record to determine if there are gaps in the data indicating that the user is due for a doctor's visit soon. As such, the analysis engine may flag the NFT 116 as having gap based on the identification and notify the user 102. In another example, the analysis engine may analyze the digital health data for a particular condition or physical aspect such as a heart condition, and determine if the user is following a healthy heart diet, using their heart medication, or attending requisite doctor's visits for their heart condition. As such, the analysis engine may use the digital health data to output an insurance policy evaluation (e.g., health insurance, life insurance). In another example, the analysis engine may receive digital health data from a population of users and analyze the digital health data to determine if the digital health data contains PII. In some embodiments, the analysis engine may determine that the digital health data contains PII and flag the NFT 116 to prevent the sale. In other embodiments, the analysis engine may determine that the digital health data does not contain PII and allow the NFT 116 to be sold on the marketplace.

In some embodiments, the NFT management system 104 may receive the output from the analysis engine and generate the NFT 116 based on the output from the analysis engine (block 806). For example, the NFT management system 104 may use the output from the analysis engine as the NFT associated content 160. In another example, the NFT management system 104 may generate the NFT 116 to contain the output from the analysis engine and the digital health data. For example, the user 102 may want to generate an NFT with all of their doctor's visits, medical records, and gaps in doctor's visits. As such, the user 102 may signal to the NFT management system 104 to generate the NFT 116 to contain the output from the analysis engine and the digital health data of the user 102. In some embodiments, the NFT management system 104 may encrypt the output from the analysis engine and the digital health data to protect the data from being public.

The NFT management system 104 may provide the digital health data or the analysis output to a storage location referred to in the NFT 116 (block 808). As described above, the storage of the NFT associated content 160 is determined based on the NFT record 150. The NFT management system 104 may provide the digital health data and the output from the analysis engine to a storage location referred to in the NFT record 150. As discussed above, the NFT associated content 106 may be stored in an off-chain storage 162. That is, the location of the off-chain storage 162 at the time the NFT 116 was minted can be specifically referred to in the NFT record 150. In other embodiments, the NFT associated content 160 may have PII removed or obscured and may be stored in IPFS or Areweave.

In some embodiments, the NFT management system 104 may provide the NFT 116 to the marketplace 704 for sale (block 810). The user 102 may decide to sell their NFT 116 containing digital health data. For example, the user 102 may decide to switch insurance providers and want to provide current digital health data to a new insurance provider. A quick and easy way to do so would be to provide the NFT 116 containing their digital health data to the new insurance provider. As such, the user may want to sell their NFT 116 to the new insurance provider. In one embodiment, the user may place their NFT 116 for sale on the marketplace 704. The marketplace 704 may be accessed by companies and institutions 108, merchants and retailers 110, financial institutions 112, or other parties interested in bidding on the NFTs 116. In some embodiments, the user 102 may set a minimum bidding price and only the NFT 116 to be sold if the bidding price may be higher than the minimum bidding price. In other embodiments, the user 102 may require the NFT management system 104 to verify that the purchaser meets a certain criteria before allowing a bid to be submitted. For example, the user 102 may only want a certain insurance provider to bid on their NFT and, as such, may require the purchaser to verify their identity with a passcode before placing a bid.

Figure 9:
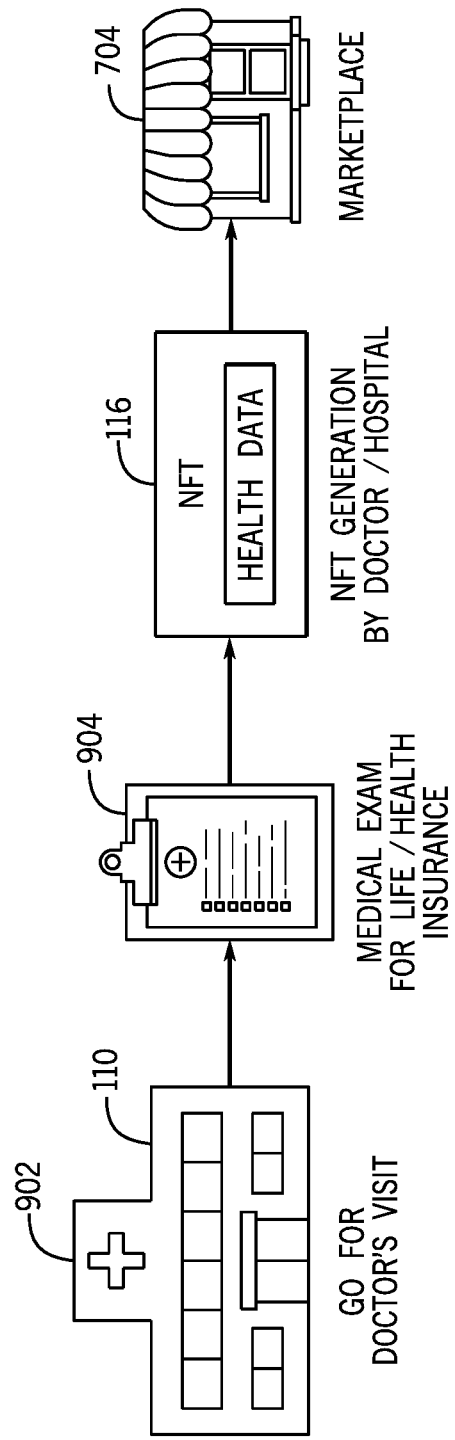
FIG. 9 is a schematic illustration of non-fungible token generation and management arrangement with respect to the example method of FIG. 8, in accordance with an embodiment.

In an embodiment, as illustrated in FIG. 9, the NFT management system 104 may receive digital health data from a health institution, such as a doctor's office, a laboratory, a clinic, a hospital, or the like. For example, a user 102 may be due for their regular check-up at a doctor's office and undergo a medical exam 904 for life insurance or health insurance purposes. As such, the doctor may record the necessary health data and store it in their network as digital health data of the user 102. In some embodiments, the user 102 may fill out an application requesting health data or answering a questionnaire regarding their current health status. The application may be entered into the NFT management system 104 and received by the analysis engine for analysis.

In some embodiments, the analysis engine may analyze the received digital health data for gaps in doctor's visits, missed medications, or other physical conditions. The analysis engine may generate an output with the missed doctor's visits, medications, or abnormal health conditions. In other embodiments, the analysis engine may analyze the received digital health data to determine whether the user 102 may be meeting predetermined health goals. The analysis engine may output an adjusted insurance policy (e.g., health insurance, life insurance).

The NFT management system 104 may use the output from the analysis engine for NFT creation. That is, the doctor's visit may result generating an NFT 116 with the digital health data collected at the doctor's office. In some embodiments, the health institution may generate the NFT 116 on behalf of the user 102 and charge the user a small amount for minting. In some embodiments, the health institution may ask the user 102 if the health data may be anonymized and pooled for machine learning purposes. As such, the health institution may remove or obscure PII from the digital, generate the NFT 116, and keep the NFT 116 in their system for storage.

In some embodiments, the NFT management system 104 may place the NFT 116 on the marketplace 704 for sale. As described above, the user 102 may decide to sell their NFT 116 containing digital health data. As such, the user 102 may access the marketplace 704 to place their NFT 116 for sale. In some embodiments, the user may set a minimum bidding price and only the NFT 116 to be sold if the bidding price may be higher than the minimum bidding price. In other embodiments, the user may require the NFT management system 104 to verify that the purchaser meets a certain criteria before allowing a bid to be submitted. For example, the user 102 may only want a certain insurance provider to bid on their NFT and, as such, may require the purchaser to verify their identity with a passcode before placing a bid.

In some embodiments, the NFT management system 104 may place the NFT 116 within the system for storage. For example, the user 102 may decide to keep their NFT 116 for a future sale. As such, the user 102 may signal to the NFT management system 104 to put the NFT 116 into storage (e.g., database, cloud storage, or the like). As such, the insurance provider may signal to the NFT management system 104 to place the NFT 116 in the storage location.

Figure 10:
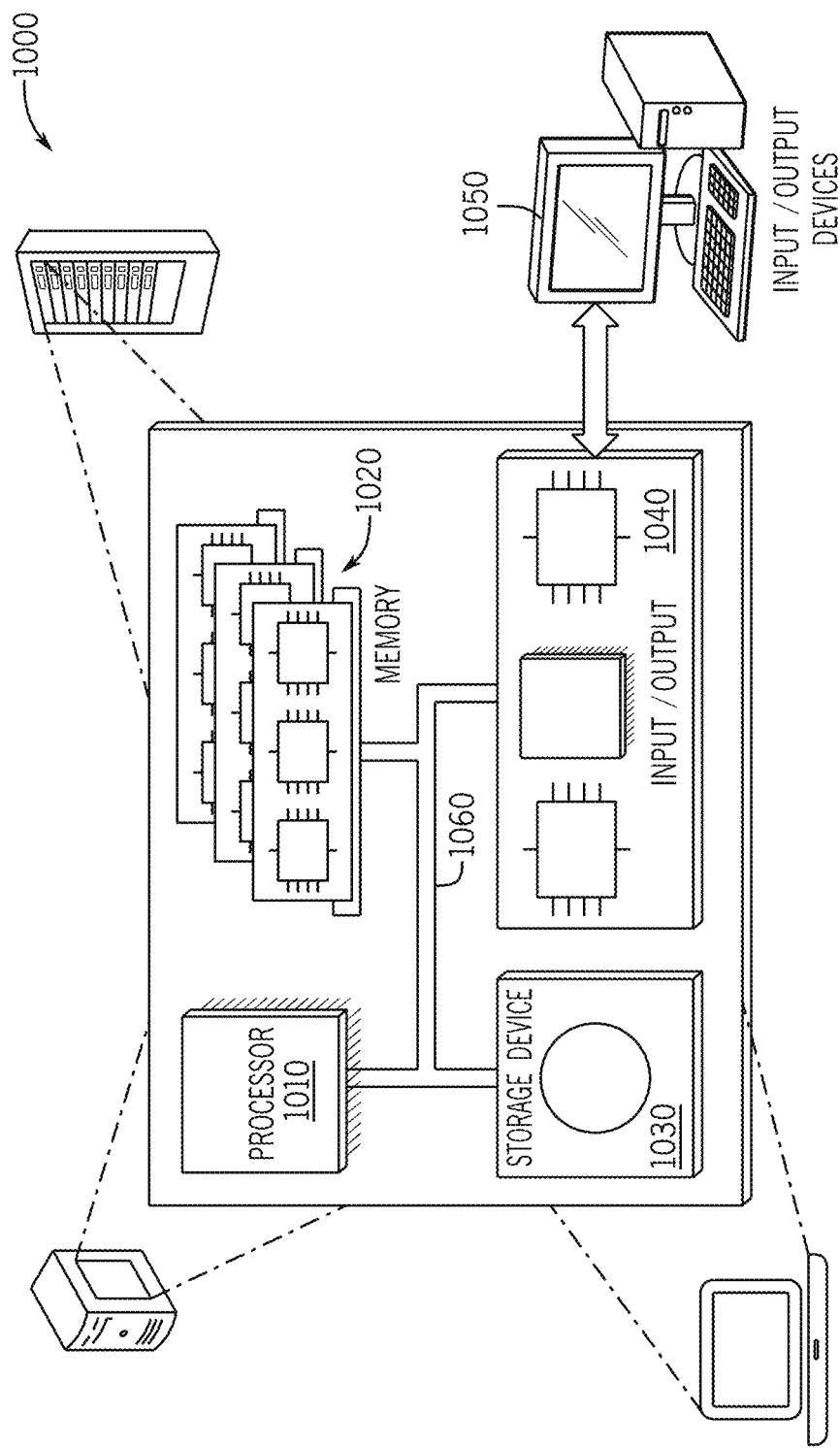
FIG. 10 is a schematic illustration of an example computing system that may be used in conjunction with the disclosed techniques, in accordance with an embodiment.

FIG. 10 illustrates an example computing system 1000 that the embodiments described herein may use to perform their respective operations. The system 1000 may be used for any of the operations described with respect to the various embodiments described herein, including the NFT management system 104 described herein. For example, the system 1000 may be included, at least in part, in one or more of computing device(s) or system(s) described herein. In certain embodiments, the system 1000 may include one or more processors 1010, one or more memory 1020, one or more storage devices 1030, and one or more input/output (I/O) devices 1050 controllable via one or more I/O interfaces 1040. The various components 1010, 1020, 1030, 1040, or 1050 may be interconnected via at least one system bus 1060, which may enable the transfer of data between the various modules and components of the system 1000.

In certain embodiments, the processor(s) 1010 may be configured to process instructions for execution within the system 1000. The processor(s) 1010 may include single-threaded processor(s), multi-threaded processor(s), or both.

The processor(s) 1010 may be configured to process instructions stored in the memory 1020 or on the storage device(s) 1030. For example, the processor(s) 1010 may execute instructions for the various software module(s) described herein. The processor(s) 1010 may include hardware-based processor(s) each including one or more cores. The processor(s) 1010 may include general purpose processor(s), special purpose processor(s), or both.

In certain embodiments, the memory 1020 may store information within the system 1000. In certain embodiments, the memory 1020 includes one or more computer-readable media. The memory 1020 may include any number of volatile memory units, any number of non-volatile memory units, or both volatile and non-volatile memory units. The memory 1020 may include read-only memory, random access memory, or both. In certain embodiments, the memory 1020 may be employed as active or physical memory by one or more executing software modules.

In certain embodiments, the storage device(s) 1030 may be configured to provide (e.g., persistent) mass storage for the system 1000. In certain embodiments, the storage device(s) 1030 may include one or more computer-readable media. For example, the storage device(s) 1030 may include a floppy disk device, a hard disk device, an optical disk device, or a tape device. The storage device(s) 1030 may include read-only memory, random access memory, or both. The storage device(s) 1030 may include one or more of an internal hard drive, an external hard drive, or a removable drive.

One or both of the memory 1020 or the storage device(s) 1030 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 1000. In certain embodiments, the CRSM may include a data store that provides storage of computer-readable instructions or other information in a non-transitory format. The CRSM may be incorporated into the system 1000 or may be external with respect to the system 1000. The CRSM may include read-only memory, random access memory, or both. One or more CRSM suitable for tangibly embodying computer program instructions and data may include any type of non-volatile memory, including but not limited to, semiconductor memory devices, such as EPROM, EEPROM, and flash memory devices: magnetic disks such as internal hard disks and removable disks: magneto-optical disks; and CD-ROM and DVD-ROM disks. In certain embodiments, the processor(s) 1010 and the memory 1020 may be supplemented by, or incorporated into, one or more application-specific integrated circuits (ASICs).

In certain embodiments, the system 1000 may include one or more I/O devices 1050. The I/O device(s) 1050 may include one or more input devices such as a key board, a mouse, a pen, a game controller, a touch input device, an audio input device (e.g., a microphone), a gestural input device, a haptic input device, an image or video capture device (e.g., a camera), or other devices. In certain embodiments, the I/O device(s) 1050 may also include one or more output devices such as a display, LED(s), an audio output device (e.g., a speaker), a printer, a haptic output device, and so forth. The I/O device(s) 1050 may be physically incorporated in one or more computing devices of the system 1000 or may be external on one or more computing devices of the system 1000.

In certain embodiments, the system 1000 may include one or more I/O interfaces 1040 to enable components or modules of the system 1000 to control, interface with, or otherwise communicate with the I/O device(s) 1050. The I/O interface(s) 1040 may enable information to be transferred in or out of the system 1000, or between components of the system 1000, through serial communication, parallel communication, or other types of communication. For example, the I/O interface(s) 1040 may comply with a version of the RS-1032 standard for serial ports, or with a version of the IEEE AA884 standard for parallel ports. As another example, the I/O interface(s) 1040 may be configured to provide a connection over Universal Serial Bus (USB) or Ethernet. In certain embodiments, the I/O interface(s) 1040 may be configured to provide a serial connection that is compliant with a version of the IEEE AA994 standard.

In certain embodiments, the I/O interface(s) 1040 may also include one or more network interfaces that enable communications between computing devices in the system 1000, or between the system 1000 and other network-connected computing systems. The network interface(s) may include one or more network interface controllers (NICs) or other types of transceiver devices configured to send and receive communications over one or more communication networks using any network protocol.

Computing devices of the system 1000 may communicate with one another, or with other computing devices, using one or more communication networks. Such communication networks may include public networks such as the Internet, private networks such as an institutional or personal intranet, or any combination of private and public networks. The communication networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In certain embodiments, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 1000 may include any number of computing devices of any type. The computing device(s) may include, but are not limited to, a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), certain embodiments are not so limited. For example, in certain embodiments, a computing device may include one or more of a virtual computing environment, a hypervisor, an emulation, or a virtual machine executing on one or more physical computing devices. In addition, in certain embodiments, two or more computing devices may include a cluster, cloud, farm, or other grouping of multiple devices that coordinate operations to provide load balancing, failover support, parallel processing capabilities, shared storage resources, shared networking capabilities, or other aspects.

All of the functional operations described herein may be realized in digital electronic circuitry, or in computer software, firmware, or hardware, including the structures described herein and their structural equivalents, or in combinations of one or more of them. The embodiments described herein may be realized as one or more computer program products, i.e., one or more modules of computer program instructions encoded on a computer-readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

Certain embodiments of the present disclosure include corresponding systems, apparatus, and computer programs that are configured to perform the actions of the methods, encoded on computer storage devices. The present disclosure also provides a computer-readable storage medium coupled to one or more processors and having instructions stored thereon which, when executed by the one or more processors, cause the one or more processors to perform operations in accordance with embodiments of the methods provided herein. The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with embodiments of the methods provided herein.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program may be deployed to be executed on one computer or on multiple computers that are located at one site or distributed across multiple sites and interconnected by a communication network.

The processes and logic flow described herein may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any appropriate kind of digital computer. Generally, a processor may receive instructions and data from a read-only memory or a random access memory or both. Elements of a computer may include a processor for performing instructions and one or more memory devices for storing instructions and data. Generally, a computer may also include, or be operatively coupled to receive data from or transfer data to, or both, one or more mass storage devices for storing data, e.g., magnetic, magneto-optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices: magnetic disks, e.g., internal hard disks or removable disks: magneto optical disks; and CD ROM and DVD-ROM disks. The processor and the memory may be supplemented by, or incorporated in, special purpose logic circuitry.

To provide for interaction with a user, certain embodiments of the system 1000 may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well: for example, feedback provided to the user may be any appropriate form of sensory feedback, e.g., visual feedback, auditory feedback, or tactile feedback; and input from the user may be received in any appropriate form, including acoustic, speech, or tactile input.

The embodiments described herein may be realized in a computing system 1000 that includes a back-end component, e.g., as a data server, or that includes a middleware component, e.g., an application server, or that includes a front-end component, e.g., a client computer having a graphical user interface or a web browser through which a user may interact with an with the system 1000, or any appropriate combination of one or more such back-end, middleware, or front end components. The components of the system 1000 may be interconnected by any appropriate form or medium of digital data communication, e.g., a communication network. Examples of communication networks include a local area network ("LAN") and a wide area network ("WAN"), e.g., the Internet.

In certain embodiments, the computing system 1000 may include clients and servers. A client and server are generally remote from each other and typically interact through a communication network. The relationship of client and server arises by computer programs running on the respective computers and having a client-server relationship to each other.

In certain embodiments, an application provides an interface for user interaction, such as a web interface or other graphical user interface (GUI). The application may interact with the smart contract(s). The interface may also be an application programming interface (API) that enables other processes to securely interact with the smart contract(s). The interface may enable a user to specify permission information, including individuals authorized to their information and/or constraints on such access. The interface may also enable the user to view information such as transaction history that is stored on the distributed ledger. In certain embodiments, a history may provide an auditable history of transactions, which are mediated by the smart contract(s) on the distributed ledger. Additionally, it should be noted that the smart contract(s) executing on a distributed ledger may make access authorization decisions based on permission information stored on the distributed ledger. In certain embodiments, the distributed ledger may be a blockchain, such as blockchain 120.

Embodiments of the present disclosure are also directed to secure device management. More particularly, embodiments of the present disclosure are directed to managing a network of devices using information and/or computer programming code on a distributed ledger system such as a blockchain. The computer programming code may include smart contracts, which may also be described as self-executing contracts, blockchain contracts, digital contracts, and/or chain code. As used herein, a smart contract refers to computer programming code executed by a distributed ledger system. For instance, smart contracts may refer to distributed programs, or distributed applications that can be used to perform the transactions and recordation in the blockchain infrastructure. Smart contracts may include data structures that may keep track of the state of the smart contract, as well as smart contract functions to interact with the smart contract. As the interactions with the smart contracts may only take place through the smart contract functions, the integrity of the state of the smart contract may be preserved. For example, smart contracts may be utilized in the exchange of information regarding users. As another example, smart contracts may be utilized in conjunction with financial transactions, such as payments or loans.

While this disclosure contains many specifics, these should not be construed as limitations on the scope of the disclosure or of what may be claimed, but rather as descriptions of features specific to particular embodiments. Certain features that are described in this disclosure in the context of separate embodiments may also be implemented in combination in a single embodiment. Conversely, various features that are described in the context of a single embodiment may also be implemented in multiple embodiments separately or in any suitable sub-combination. Moreover, although features may be described herein as acting in certain combinations and even initially claimed as such, one or more features from a claimed combination may in certain embodiments be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain embodiments, multitasking and parallel processing may be advantageous. Moreover, the separation of various system components in the embodiments described herein should not be understood as requiring such separation in all embodiments, and it should be understood that the described program components and systems may generally be integrated together in a single software product or packaged into multiple software products.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

The invention claimed is:

1. A health data management system using non-fungible tokens, the system comprising:
a memory storing executable instructions;
a processor configured to execute the instructions to:
receive digital health data;
receive a request to generate a non-fungible token using the digital health data via a display;
confirm the non-fungible token as an asset on a distributed ledger and store the digital health data in a storage location outside of the distributed ledger based on the request;
transmit the digital health data to an analysis engine;
generate associated content based on an output of the analysis engine; and
generate a non-fungible token comprising:
the associated content, wherein the associated content further comprises metadata associated with the digital health data; and
a record in the distributed ledger comprising the storage location of the digital health data.

2. The system of claim 1, wherein the digital health data is received from a medical institution.

3. The system of claim 1, wherein the digital health data is received from a mobile device of a user, and wherein the digital health data is digital health data of the user.

4. The system of claim 1, wherein the memory is the storage location of the digital health data.

5. The system of claim 1, wherein the record in the distributed ledger comprises additional digital health data.

6. The system of claim 1, wherein the processor is further configured to execute the instructions to:
access a medical record of a user;
identify a gap in the medical record; wherein the gap is a missed doctor's appointment, laboratory test, prescription, or a combination thereof; and
flag the non-fungible token as having the gap based on the identifying.

7. The system of claim 1, wherein the processor is further configured to execute instructions to:
determine that the digital health data includes personal identifying information; and
remove or obscure the personally identifiable information (PII) before generating the non-fungible token.

8. The system of claim 7, wherein the system is configured to execute the instructions to manage non-fungible token transactions, and wherein the processor is configured to place the non-fungible token within a marketplace for marketplace transactions in response determining that the non-fungible token does not comprise the PII.

9. The system of claim 1, wherein the system is configured to manage non-fungible token transactions, and wherein the processor is further configured to execute the instructions to flag the non-fungible token as being ineligible for marketplace transactions based on determining that the digital health data includes personal identifying information.

10. The system of claim 1, wherein the processor is further configured to execute instructions to:
  determine that the digital health data meets predetermined conditions; wherein the predetermined conditions are based on factors such as age, health conditions, diet, medication, or a combination thereof;
  generate insurance evaluation data based on the determination; and
  generate the non-fungible token based on the insurance evaluation data.

11. The system of claim 10, wherein the processor is further configured to execute the instructions to receive additional digital health data and update the associated content of the non-fungible token based on the additional digital health data.

12. The system of claim 11, comprising a health tracking device that comprises a mobile device of a user, wherein the digital health data is health data of the user.

13. The system of claim 1, wherein the processor is further configured to execute instructions to:
  prompt entry of a passcode; and
  prompt entry of a bid for the non-fungible token eligible for marketplace transactions in response to determining a match between the passcode and a stored passcode.

14. The system of claim 1, wherein the digital health data comprises medical charts, medical evaluations, sleep data, fitness data, heart rate data, or any combination thereof.

15. The system of claim 1, wherein the processor is further configured to execute instructions to encrypt the digital health data prior to generating minting the non-fungible token.

16. The system of claim 1, wherein the digital health data comprises aggregated digital health data associated with population of users.

17. The system of claim 16, wherein the processor is further configured to:
  identify a subset of the aggregated digital health data based on metadata of the aggregated digital health data, attributes of the aggregated digital health data, or both; and
  store the subset of the aggregated digital health data in the storage location outside of the distributed ledger.

18. The system of claim 16, wherein the record comprises the metadata of the aggregated digital health data and a link associated with the storage location, and wherein the processor is further configured to identify the aggregated health data based on the metadata, the link, or both.

19. The system of claim 1, wherein the analysis engine is configured to determine whether a user is meeting health goals based on the digital health data, wherein the health goals are stored in the database and associated with the user.

* * * * *